United States Patent [19]
Kalchauer et al.

[11] Patent Number: 5,981,784
[45] Date of Patent: Nov. 9, 1999

[54] PROCESS FOR PREPARING ORGANOCHLOROSILANES

[75] Inventors: Wilfried Kalchauer, Burghausen; Herbert Straussberger; Willi Streckel, both of Mehring/Öd, all of Germany

[73] Assignee: Wacker-Chemie GmbH, Munchen, Germany

[21] Appl. No.: 09/282,688

[22] Filed: Mar. 31, 1999

[30] Foreign Application Priority Data

Apr. 21, 1998 [DE] Germany .......................... 198 17 775

[51] Int. Cl.$^6$ ....................................... C07F 7/16
[52] U.S. Cl. ............................ 556/472; 556/473
[58] Field of Search ..................... 556/472, 473

[56] References Cited

U.S. PATENT DOCUMENTS

| | | |
|---|---|---|
| 4,656,301 | 4/1987 | Prud'Homme et al. ................. 556/472 |
| 4,661,613 | 4/1987 | Prud'Homme et al. ................. 556/472 |
| 4,864,044 | 9/1989 | Lewis et al. . |
| 4,962,220 | 10/1990 | Halm et al. .............................. 556/473 |
| 4,966,986 | 10/1990 | Halm et al. .............................. 556/473 |
| 5,117,030 | 5/1992 | Cattoz et al. ........................... 556/472 |
| 5,306,328 | 4/1994 | Streckel et al. . |
| 5,625,088 | 4/1997 | Kalchauer ............................... 556/473 |
| 5,874,604 | 2/1999 | Steiner et al. .......................... 556/472 |

OTHER PUBLICATIONS

Lieske et al., "Silicon for Chemical Industry", Geiranger–Norway, Jun. 8–10, 1994, pp. 129–135.

H.A. Oye and H. Rong, "Silicon for Chemical Industry", Geiranger–Norway, Jun. 16–18, 1992, pp. 111–118.

*Primary Examiner*—Paul F. Shaver
*Attorney, Agent, or Firm*—Brooks & Kushman P.C.

[57] ABSTRACT

In the direct synthesis of methylchlorosilanes by reacting methyl chloride with a catalyst composition which comprises silicon, copper catalyst, zinc promoters and tin promoters and/or antimony promoters, a catalyst composition is used which was activated in advance by treatment with HCl under specific activation conditions.

13 Claims, No Drawings

PROCESS FOR PREPARING ORGANOCHLOROSILANES

TECHNICAL FIELD

The invention relates to a process for the direct synthesis of methylchlorosilanes by the Müller-Rochow method, in which the catalyst composition is activated by an HCl treatment before the reaction.

BACKGROUND ART

In the Müller-Rochow direct synthesis, methyl chloride is reacted with silicon in the presence of a copper catalyst and suitable promoters to form methylchlorosilanes. In this process, both the highest possible productivity (amount of silanes formed per unit time and amount of silicon used) and the highest selectivity, based on the target product dimethyldichlorosilane, is demanded. Dimethyldichlorosilane is required, for example, for preparing linear polysiloxanes.

Despite the great economic importance of the direct synthesis, its scientific background has still not been completely studied. According to Lieske et al. in SILICONE FOR CHEMICAL INDUSTRY, Geiranger-Norway, Jun. 16–18, 1992, owing to the participation of three solids in the reaction, that is to say silicon, catalyst and promoters, the reproducibility of the experiments is frequently poor. In practice, different batches of the direct synthesis, despite identical material parameters and reaction parameters, proceed with variable results.

The direct synthesis can be carried out batchwise or continuously, although in industrial production only the continuous variant is employed. The continuous direct synthesis is carried out in fluidized-bed reactors in which methyl chloride is used simultaneously as fluidizing medium and reactant. The silicon required is ground in advance to give a powder of particle size from 20 to 700 $\mu$m and mixed with copper catalyst and promoters to form the catalyst composition.

Before the continuous direct synthesis production campaign, there is provided a "reactor heat-up phase", in which the catalyst composition is heated to reaction temperature. A continuous direct synthesis production campaign begins with the "induction phase". At the start of the induction phase, methyl chloride is introduced into the heated catalyst composition. This is followed by the "start phase" in which the crude silane formation is initiated. The reaction initially proceeds at low selectivity and reactivity. The stable "production phase" is then reached. The production campaign ends when methyl chloride is no longer introduced into the catalyst composition.

During the continuous operation of a reactor in a production campaign, after a substantially stable production phase, the production rate, based on methylchlorosilanes, and the selectivity, based on the target product dimethyldichlorosilane, both decrease. Therefore, the production campaign must be terminated after a certain time. As a result, a production campaign therefore usually lasts from only a few days to several weeks.

The reactor, after termination of a production campaign, is emptied, refilled with silicon, copper catalyst and promoters, and again brought to reaction conditions. It can be seen from the foregoing, that increasing the production rate and prolonging the duration of the production campaign, while retaining the same selectivity, increases the economic efficiency of the direct synthesis.

Activating the catalyst composition before the reaction with methyl chloride by a preliminary reaction with HCl is disclosed, for example, by U.S. Pat. No. 4,864,044. In the examples there, a process is described in which silicon, copper catalyst with or without tin promoter, but in the absence of zinc promoters, can be activated by HCl at approximately 325° C. The disadvantages of this type of activation are that zinc or zinc compounds can be added only after the activation, since zinc forms readily sublimable zinc chloride with HCl under the specified reaction conditions and can thus be removed from the catalyst composition during the activation; a separate reactor is required for the activation and the reaction products of the activation were, in particular, trichlorosilane and tetrachlorosilane, are unwanted by-products of the methylchlorosilane synthesis; at least from 1 to 2% of the silicon raw material used is consumed by the activation; and a relatively high activation temperature is required.

SUMMARY OF THE INVENTION

It is an object of the present invention to provide a process for the direct synthesis of methylchlorosilanes by the Müller-Rochow process, in which, while retaining the selectivity with respect to dimethyldichlorosilane, the productivity can be increased without the abovementioned disadvantages of U.S. Pat. No. 4,864,044 becoming noticeable.

DESCRIPTION OF THE PREFERRED EMBODIMENTS

The invention relates to a process for the direct synthesis of methylchlorosilanes by reacting methyl chloride with a catalyst composition which comprises silicon, copper catalyst, zinc promoters and tin promoters and/or antimony promoters, in which use is made of a catalyst composition which has been activated by treatment with HCl under specific reaction parameters before being used in the reaction campaign.

The catalyst composition is activated by HCl during the reactor heat-up phase, the HCl activation being completed below the temperature at which the reaction of silicon with HCl to form hydrochlorosilanes proceeds to a significant extent or at which a melt phase of CuCl and $ZnCl_2$ can form. The melting point of a eutectic mixture of CuCl and $ZnCl_2$ is approximately 235° C., according to H. A. Oye, SILICON FOR THE CHEMICAL INDUSTRY II, Loen-Norway, June, 1994.

The catalyst composition is activated by HCl preferably at at least 60° C., in particular at least 110° C., since under these conditions, any reaction water formed by the activation can rapidly be discharged from the system. The temperature is preferably at most 200° C., particularly preferably at most 180° C.

HCl can be used alone or in a mixture with other substances which are gaseous under activation conditions. In a preferred embodiment, HCl is added to the gas stream which is passed through the reactor in the reactor heat-up phase. This can be, for example, an inert gas, such as nitrogen or argon, or the later reaction gas, in particular methyl chloride.

The concentration of added HCl in the gas stream principally depends on the metering duration, the temperature at which addition takes place and the absolute amount of HCl added. In a preferred embodiment, HCl is added in an amount of from 1 to 30% by volume to the gas stream which is passed through the catalyst composition.

The HCl metering period principally depends on the temperature at which the addition takes place, and also on the absolute amount added. It can be in the range from a few minutes to a few hours. Insufficient addition of HCl leads to a reduced increase in productivity.

The total amount of gas which is passed through the reactor during the heat-up phase depends on the respective reactor dimensions and on the particle sizes of the raw materials used. The gas stream preferably serves as fluidizing medium.

The catalyst composition is prepared by simple mixing of the individual components at room temperature. A subsequent thermal treatment of the catalyst composition with the exclusion of HCl prior to introduction into the reactor is possible, but is not carried out in the preferred embodiment.

In the process according to the invention, in a preferred embodiment use is made of silicon in a particle size of below 700 μm and greater than 20 μm, particularly preferably in a particle size below 500 μm and greater than 50 μm. The silicon customarily used has a purity of >98%.

In the process according to the invention, use is made of a) copper, preferably in the form of copper oxide mixtures, in the form of copper(II) oxide, in the form of CuCl or in the form of $CuCl_2$. In the case of mixed oxides of the general formula $CuO_x$, x has a value of from 0.6 to 1, preferably a value of at least 0.7. The copper oxides can be prepared, for example, by the process described in U.S. Pat. No. 5,306,328, in which the degree of oxidation can be set specifically by the drying temperature and the residence time at this temperature. Preferably, use is made of from 0.5 to 10% by weight, in particular from 0.7 to 7% by weight, of copper catalyst, based on metallic copper and silicon, particular preference is given to from 1 to 5% by weight.

In the process according to the invention, use is made of b) zinc, preferably in the form of metallic zinc, alternatively as an alloy with copper, tin and/or antimony, zinc oxide or zinc chloride. The amount of zinc used is preferably from 0.5 to 60% by weight, in particular from 2 to 40% by weight, of Zn, based on copper, particularly preferably use is made of from 5 to 30% by weight of Zn.

In the process according to the invention, use is made of c) antimony and/or tin, preferably as metals. The amount of antimony or tin used is preferably from 200 to 8000 ppm, in particular from 300 to 4000 ppm, based on the copper used, particularly preferably use is made of from 500 to 3000 ppm of antimony and/or tin.

In the examples below, unless otherwise stated, all amounts are based on the mass; all pressures are 0.10 MPa (absolute); all temperatures are 20° C.; and silane M2=dimethyldichlorosilane.

The results for the reaction of silicon with chloromethane in the presence of suitable catalysts are dependent, not only on the constitution of the catalyst composition, but also on the structure of the experimental plant and the experimental procedure. To eliminate the two last-mentioned parameters and to be able to demonstrate clearly the advantages of the invention, the experiments described in Examples 1 to 13 were carried out according to the following standardized procedure.

Silicon Powder

Granules from Fesil ASA, Norway; particle size in the range from 70 to 240 μm.

Copper Oxide

Prepared in accordance with U.S. Pat. No. 5,306,328, Example 5.

All other chemicals used are commercially available in the chemicals industry, e.g. from Fluka Chemie GmbH, Germany.

Experimental Plant

Laboratory fluidized-bed reactor (vertical glass tube having an inner diameter of 25 mm and a height of 500 mm) equipped with heating coil, gas distribution frit, distillation bridge with brine cooling and receiver flask.

Standardized Procedure 120 g of silicon are mixed intimately with the copper catalyst, zinc promoter and 8 mg of tin powder, charged into the reactor and heated to 340° C. under a nitrogen stream of 40 l/h. 40 l/h of methyl chloride are then passed through the reactor and the catalyst composition is heated to 395° C. After a certain induction time, the silane formation starts (start-up time), the reaction temperature is decreased to 360° C. and 50 ml of methylchlorosilanes are collected (start phase).

Production Phase

A further 30 ml of methylchlorosilanes are then collected. The time for formation of this 30 ml of silanes is termed the production phase, and the production rate (PR2) is calculated from the equation:

$$PR2 = \frac{\text{mg of methylchlorosilanes in the production phase}}{\text{silicon surface area} \times \text{minutes in the production phase}}$$

The silane composition of the 30 ml of methylchlorosilanes was determined in weight percent by GC analysis.

Comparative Examples C1–C5

Not According to the Invention

These comparison examples illustrate reaction courses of non-activated catalyst compositions. The procedure used is in accordance with the standard process without HCl activation. The results are summarized in Tables 1a and 1b below:

TABLE 1a

| Example | Cu Catalyst | Zn Promoter |
|---------|-------------|-------------|
| C1 | 6.0 g CuO | 1.0 g ZnO |
| C2 | 6.0 g CuO | 1.7 g $ZnCl_2$ |
| C3 | 7.5 g CuCl | 1.7 g $ZnCl_2$ |
| C4 | 3.0 g CuO | 1.7 g $ZnCl_2$ |
| C5 | 3.0 g CuO | 1.0 g ZnO |

TABLE 1b

| Example | Start-Up Time | PR2 | % By Weight Of Silane M2 |
|---------|---------------|-----|--------------------------|
| C1 | 30 minutes | 119 | 86.4 |
| C2 | 27 minutes | 174 | 87.8 |
| C3 | 18 minutes | 102 | 83.0 |
| C4 | 17 minutes | 159 | 83.0 |
| C5 | 20 minutes | 116 | 85.0 |

EXAMPLES 1–3

According to the Invention

The procedure of Example C1 is followed, with the modification that during the heat-up phase, HCl is added to the nitrogen gas stream. The conditions and results are set forth in Tables 2a and 2b below:

TABLE 2a

| Example | HCl (1/h) | Period (minutes) | Temperature Range |
|---|---|---|---|
| 1 | 12 | 30 | 180° C. |
| 2 | 3 | 10 | 120–180° C. |
| 3 | 3 | 60 | 120–180° C. |

TABLE 2b

| Example | HCl (1/h) | PR2 | Temperature Range |
|---|---|---|---|
| 1 | 15 minutes | 280 | 83.0% |
| 2 | 13 minutes | 239 | 85.2% |
| 3 | 14 minutes | 168 | 88.9% |

EXAMPLE 4

According to the Invention

The procedure of Example C2 is followed, with the modification that during the heat-up phase, HCl is added to the nitrogen gas stream at a rate of 3 l/h for 10 minutes in the temperature range of 120–180° C. The start-up time is 10 minutes, and the production rate, PR2 is 220. The percent by weight of silane M2 produced is 88.3%.

EXAMPLE 5

According to the Invention

The procedure of Example C3 is followed, with the modification that during the heat-up phase, HCl is added to the nitrogen gas stream at a rate of 3 l/h for 10 minutes in the temperature range of 120–180° C. The start-up time is 3 minutes, and the production rate, PR2 is 126. The percent weight of silane M2 produced is 84.9%.

EXAMPLE 6

According to the Invention

The procedure of Example C4 is followed, with the modification that during the heat-up phase, HCl is added to the nitrogen gas stream at a rate of 3 l/h for 10 minutes in the temperature range of 120–180° C. The start-up time is 12 minutes, the production rate, PR2 is 203, and the percent by weight of silane M2 produced is 83.7%.

EXAMPLE 7

According to the Invention

The procedure of Example C5 is followed, with the modification that during the heat-up phase, HCl is added to the nitrogen gas stream at a rate of 3 l/h for 10 minutes in the temperature range of 120–180° C. The start-up time is 14 minutes, and the production rate, PR2 is 135, and the percent weight of silane M2 produced is 85.0%.

What is claimed is:

1. A process for the direct synthesis of methylchlorosilanes by reacting methyl chloride with a catalyst composition which comprises silicon, copper catalyst, zinc promoters, and tin promoters and/or antimony promoters, the improvement comprising selecting, as said catalyst composition, a catalyst composition which comprises silicon, copper catalyst, zinc promoters, and tin and/or antimony promoters activated by treatment with HCl before being used in the reaction campaign.

2. The process of claim 1 wherein said catalyst is activated at an activation temperature below that at which a melt phase of CuCl and $ZnCl_2$ can form.

3. The process as claimed in claim 1, in which the activation takes place at from 110° C. to 200° C.

4. The process as claimed in claim 1, in which HCl is added to the gas stream which is passed through the reactor in the reactor heat-up phase.

5. The process as claimed in claim 2, in which HCl is added to the gas stream which is passed through the reactor in the reactor heat-up phase.

6. The process as claimed in claim 3, in which HCl is added to the gas stream which is passed through the reactor in the reactor heat-up phase.

7. The process as claimed in claim 4, in which HCl is added to the gas stream in an amount of from 1 to 30% by volume.

8. The process as claimed in claim 5, in which HCl is added to the gas stream in an amount of from 1 to 30% by volume.

9. The process as claimed in claim 6, in which HCl is added to the gas stream in an amount of from 1 to 30% by volume.

10. The process of claim 1 wherein said catalyst composition is activated in the same reaction vessel which will be used in a subsequent production campaign employing said catalyst composition.

11. The process of claim 1 wherein the production rate is higher than the production rate obtained under the same conditions but without activation of said catalyst composition with HCl.

12. The process of claim 1 wherein the selectivity to dimethyldichlorosilane is higher than the selectivity to dimethyldichlorosilane obtained under the same conditions but without activation of said catalyst composition with HCl.

13. The process of claim 1 wherein the production rate and selectivity to dimethyldichlorosilane are higher than the production rate and selectivity to dimethyldichlorosilane obtained under the same conditions but without activation of said catalyst composition with HCl.

* * * * *